United States Patent
Kwon et al.

(10) Patent No.: US 11,692,191 B2
(45) Date of Patent: Jul. 4, 2023

(54) METHOD FOR SEPARATING, CAPTURING, ANALYZING AND RETRIEVING CELLS AND CELL PRODUCTS BY USING MICROSTRUCTURE

(71) Applicant: SEOUL NATIONAL UNIVERSITY R&DB FOUNDATION, Seoul (KR)

(72) Inventors: Sung Hoon Kwon, Seoul (KR); Jun Hoi Kim, Seoul (KR); Seo Hee Chang, Suwon-si (KR); Ok Ju Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 155 days.

(21) Appl. No.: 16/612,880

(22) PCT Filed: May 14, 2018

(86) PCT No.: PCT/KR2018/005507
§ 371 (c)(1),
(2) Date: Nov. 12, 2019

(87) PCT Pub. No.: WO2018/208135
PCT Pub. Date: Nov. 15, 2018

(65) Prior Publication Data
US 2020/0199583 A1    Jun. 25, 2020

(30) Foreign Application Priority Data

May 12, 2017 (KR) .......................... 10-2017-0059325

(51) Int. Cl.
| | | |
|---|---|---|
| *C12N 15/10* | (2006.01) | |
| *B01J 19/00* | (2006.01) | |
| *B01L 3/00* | (2006.01) | |
| *C40B 40/00* | (2006.01) | |
| *C40B 60/12* | (2006.01) | |
| *G01N 33/543* | (2006.01) | |

(52) U.S. Cl.
CPC ...... *C12N 15/1093* (2013.01); *B01J 19/0046* (2013.01); *B01L 3/5027* (2013.01); *C40B 40/00* (2013.01); *C40B 60/12* (2013.01); *G01N 33/54306* (2013.01); *G01N 33/54386* (2013.01); *B01J 2219/00644* (2013.01); *B01J 2219/00743* (2013.01)

(58) Field of Classification Search
CPC .............. C12N 15/1093; B01J 19/0046; B01J 2219/00644; B01J 2219/00743; B01L 3/5027; C40B 40/00; C40B 60/12; G01N 33/54306; G01N 33/54386
See application file for complete search history.

(56) References Cited

U.S. PATENT DOCUMENTS

2013/0190206 A1    7/2013   Leonard et al.

FOREIGN PATENT DOCUMENTS

| KR | 1020050119419 A | 12/2005 |
|---|---|---|
| KR | 1020130042857 A | 4/2013 |
| KR | 1020130100149 A | 9/2013 |
| KR | 1020140111224 A | 9/2014 |
| KR | 1020160019913 A | 2/2016 |
| KR | 101672654 B1 | 11/2016 |
| KR | 1020170047182 A | 5/2017 |

OTHER PUBLICATIONS

Couston et al. "Adsorption behavior of a human monoclonal antibody at hydrophilic and hydrophobic surfaces" mAbs 5:1, 1-14; Jan./Feb. 2013. (Year: 2013).*
Joung et al. "ITO-coated glass/polydimethylsiloxane continuous-flow PCR chip", Proceedings of the 2nd IEEE International Conference on Nano/Micro Engineered and Molecular Systems, Jan. 16-19, 2007, Bangkok, Thailand; pp. 691-694 (Year: 2007).*
International Search Report of PCT/KR2018/005507, dated Feb. 8, 2019, English translation.
Dan Gao et al, A microfluidic approach for anticancer drug analysis based on hydrogel encapsulated tumor cells, Analytica Chimica Acta, Mar. 7, 2010, pp. 7-14, vol. 665, Elsevier, Amsterdam, Netherlands.

\* cited by examiner

*Primary Examiner* — Nancy J Leith
*Assistant Examiner* — Jessica D Parisi
(74) *Attorney, Agent, or Firm* — STIP Law Group, LLC

(57) ABSTRACT

The present invention relates to a technique for genomic library screening and provides a method for separating, capturing, analyzing, and retrieving cells and cell products by using a microstructure that can be preferentially applied to the field of antibody engineering for the development of new therapeutic antibodies and can be extensively applied to multiple genetic/phenotypic analysis of various biochemical molecules, for example, in the field of protein engineering and metabolic engineering.

21 Claims, 9 Drawing Sheets

[Fig. 1]
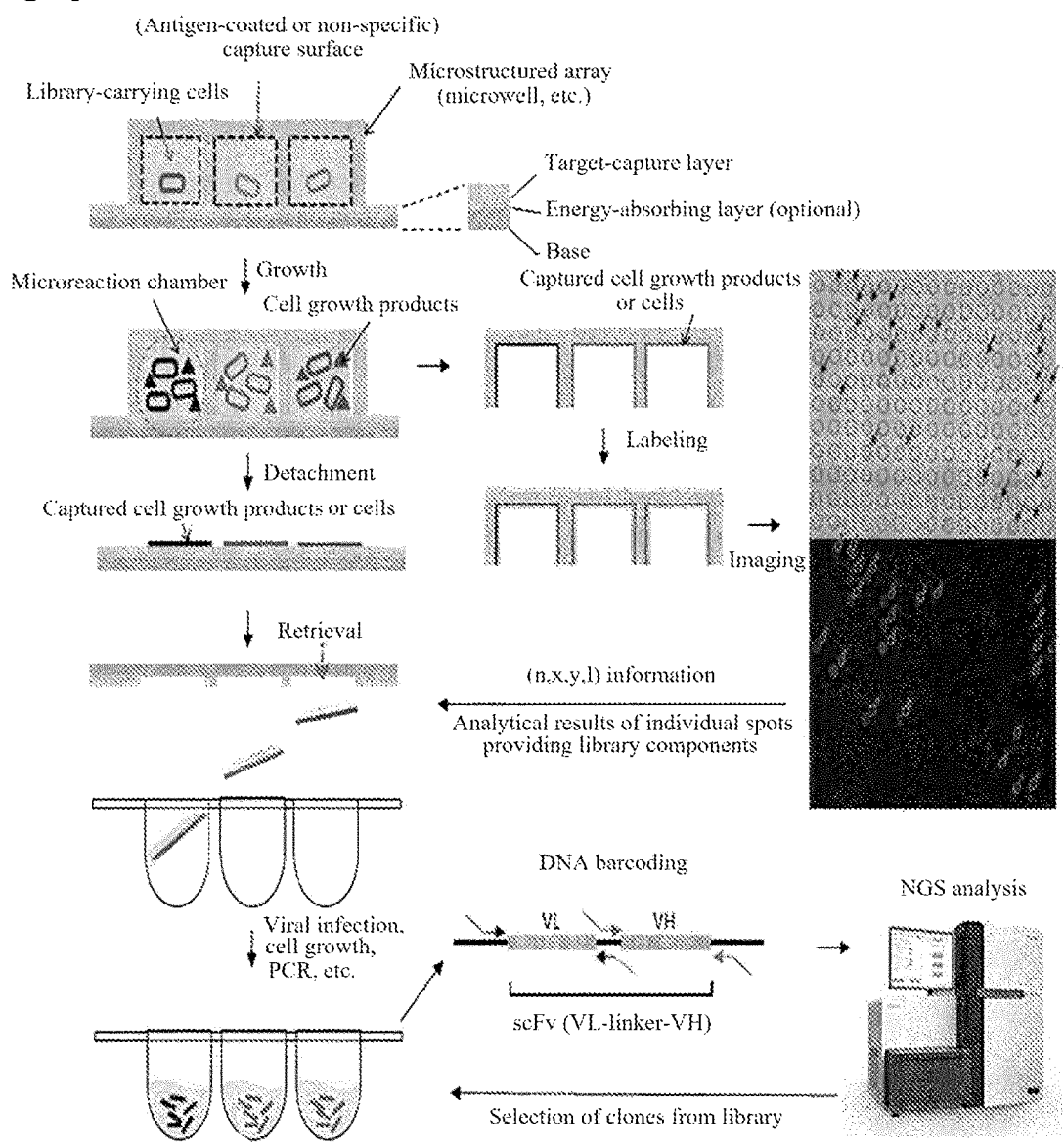

[Fig. 2]
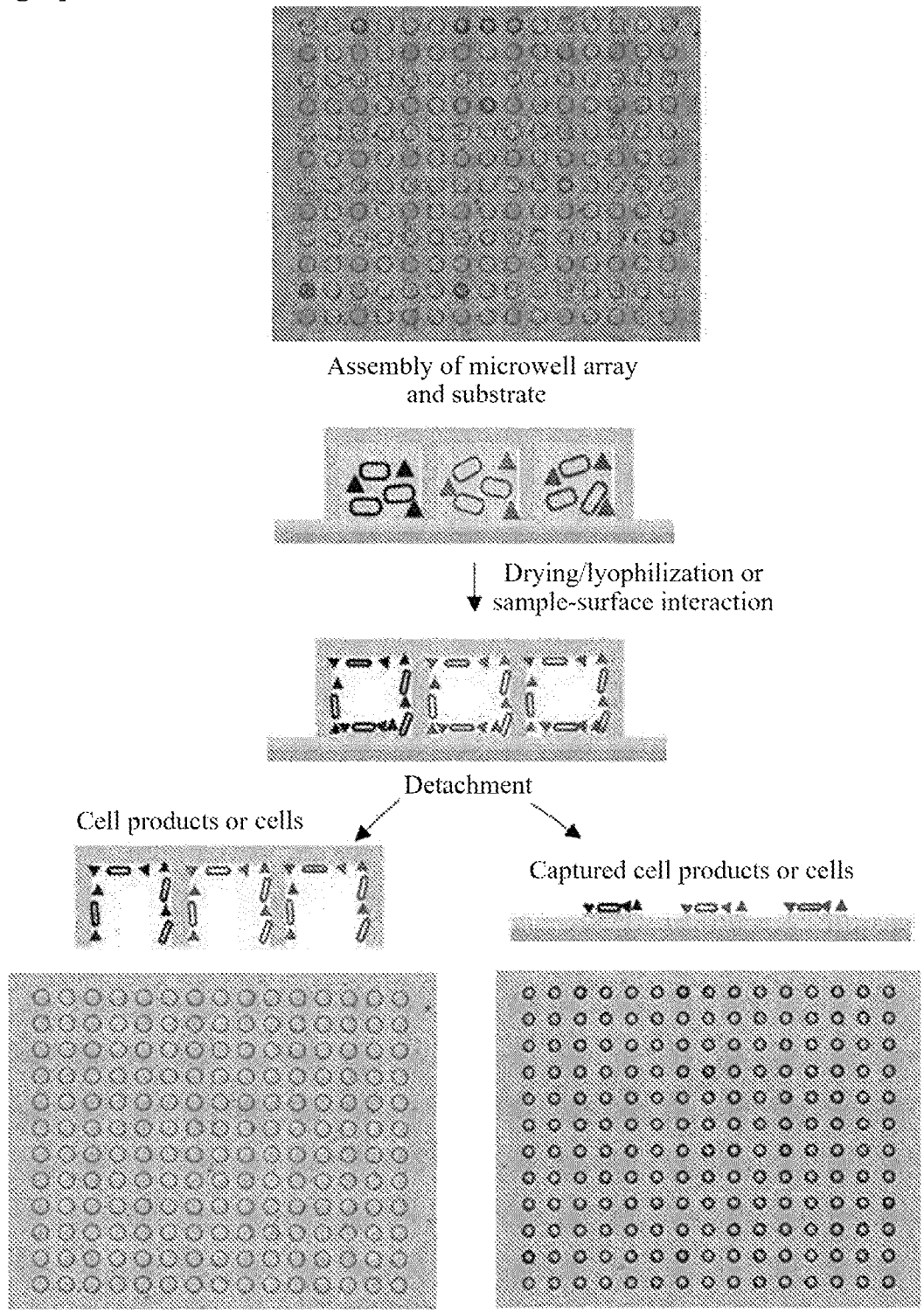

[Fig. 3]
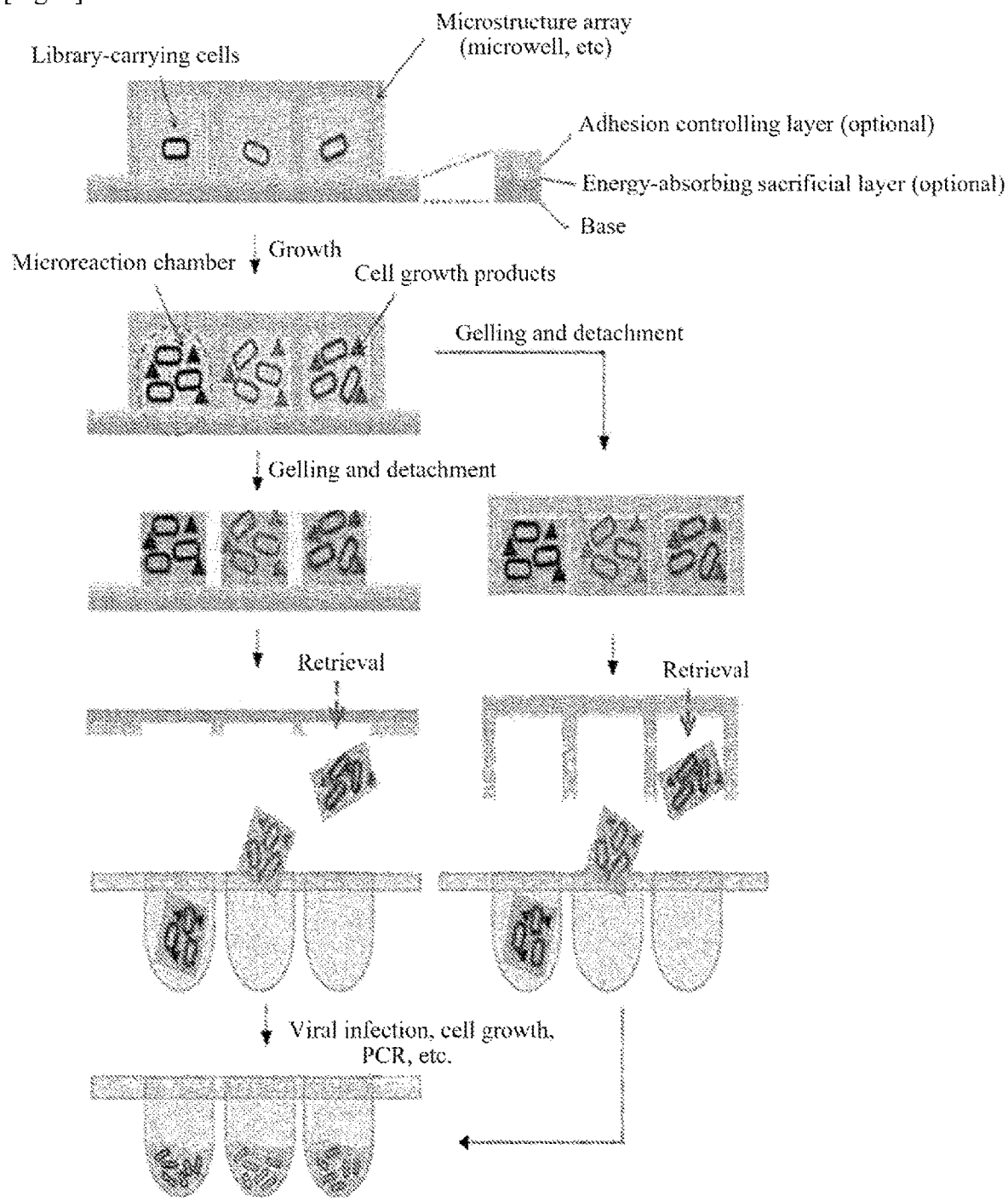

[Fig. 4]
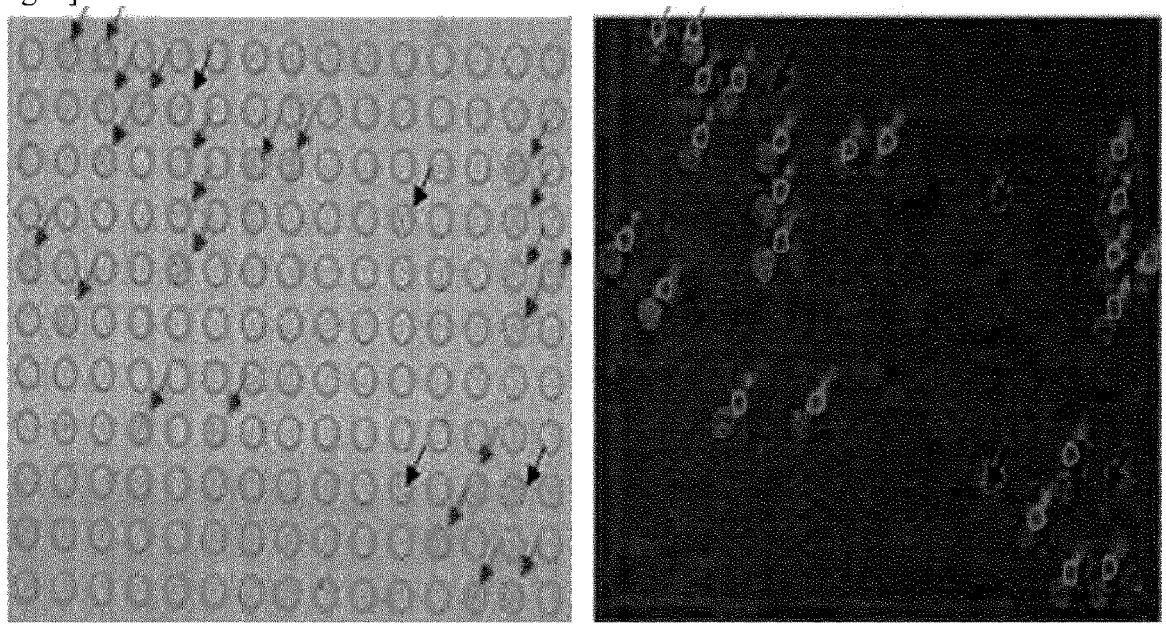

[Fig. 5]
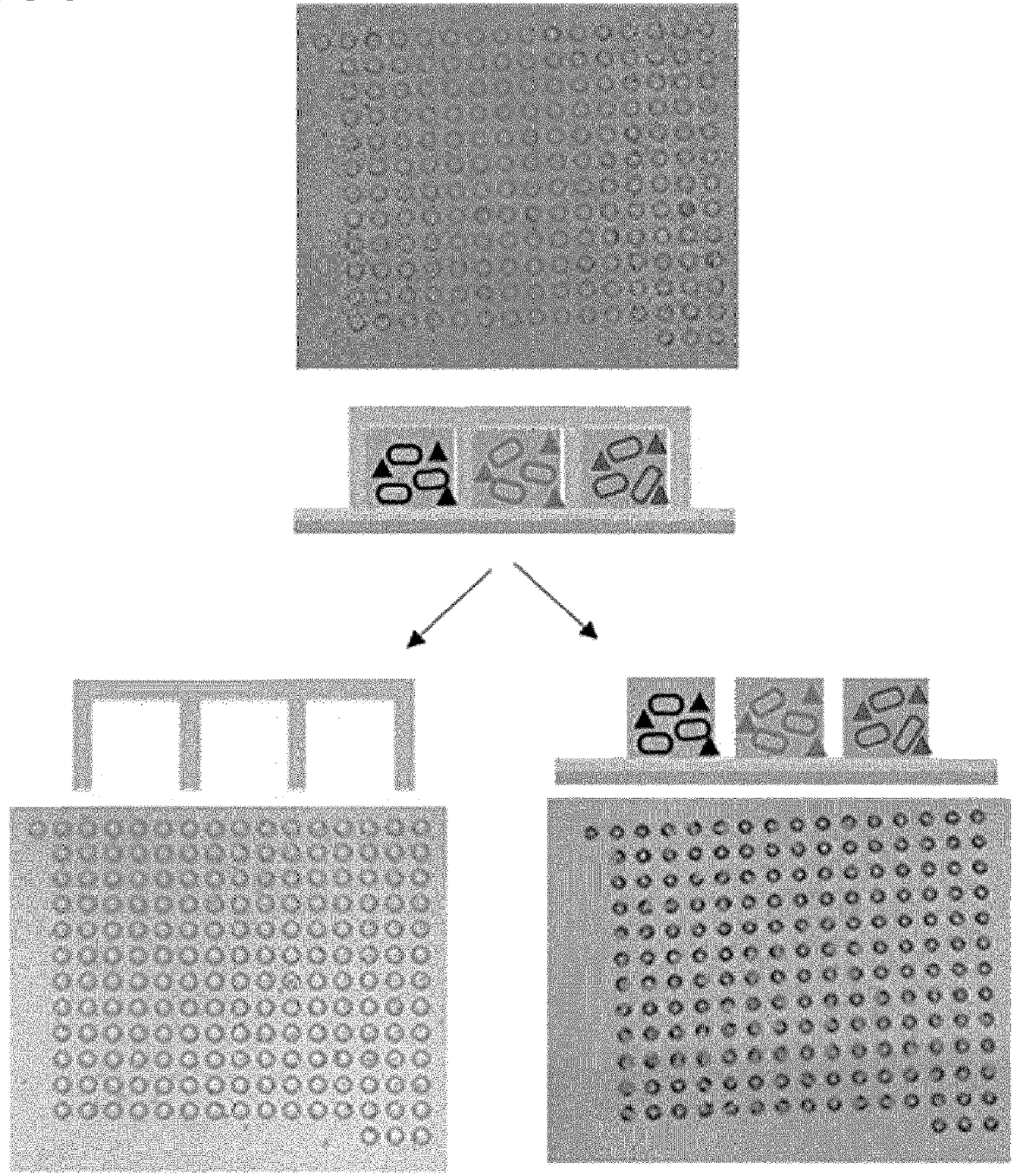

[Fig. 6]
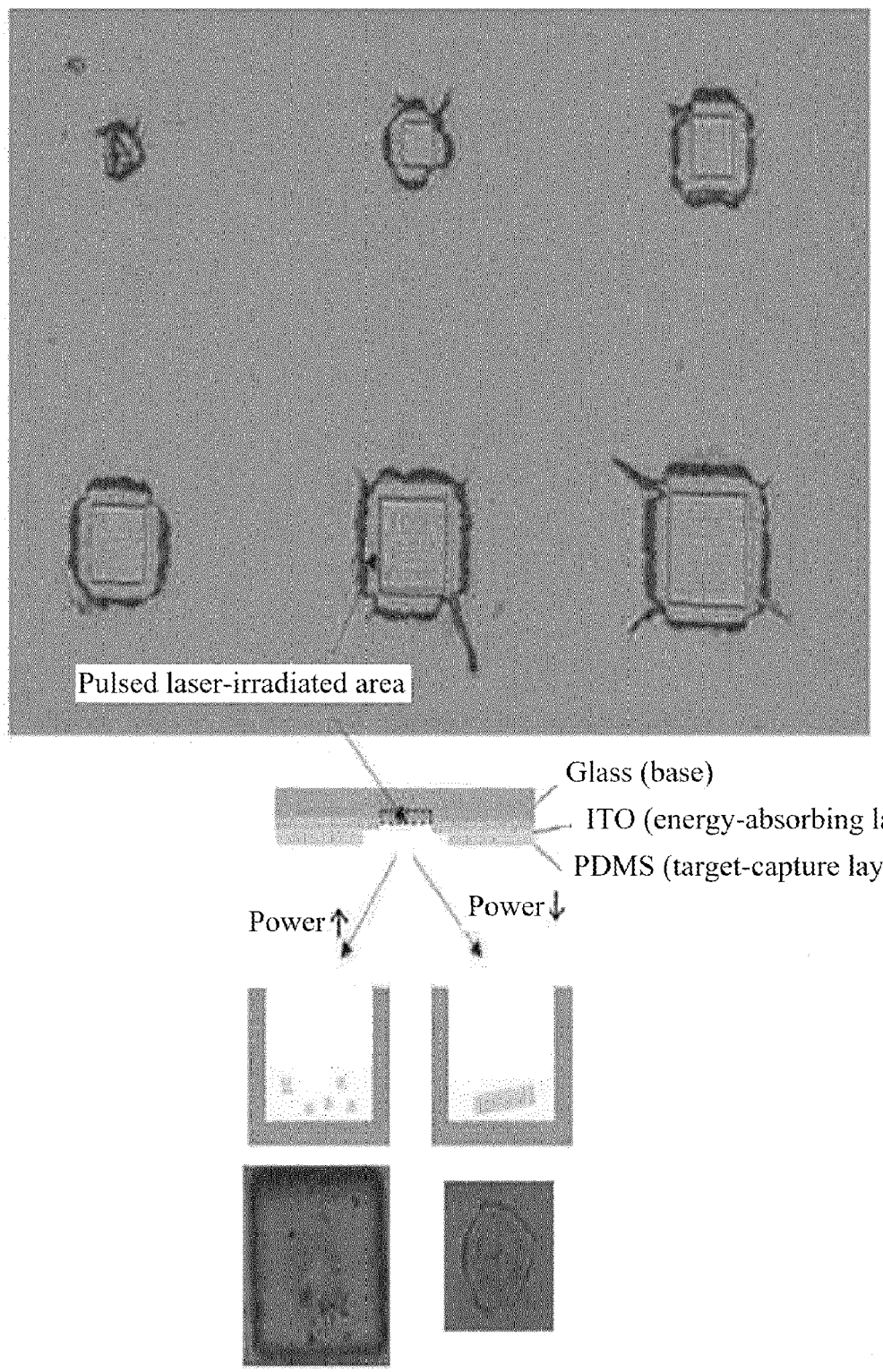

[Fig. 7]
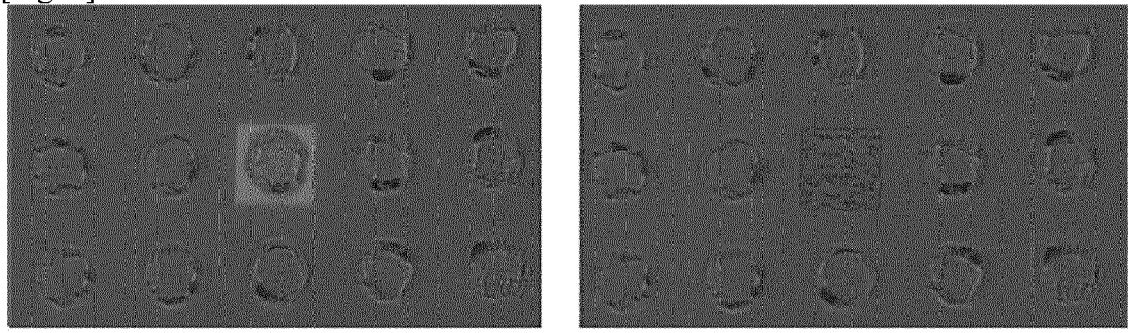
[Fig. 8]
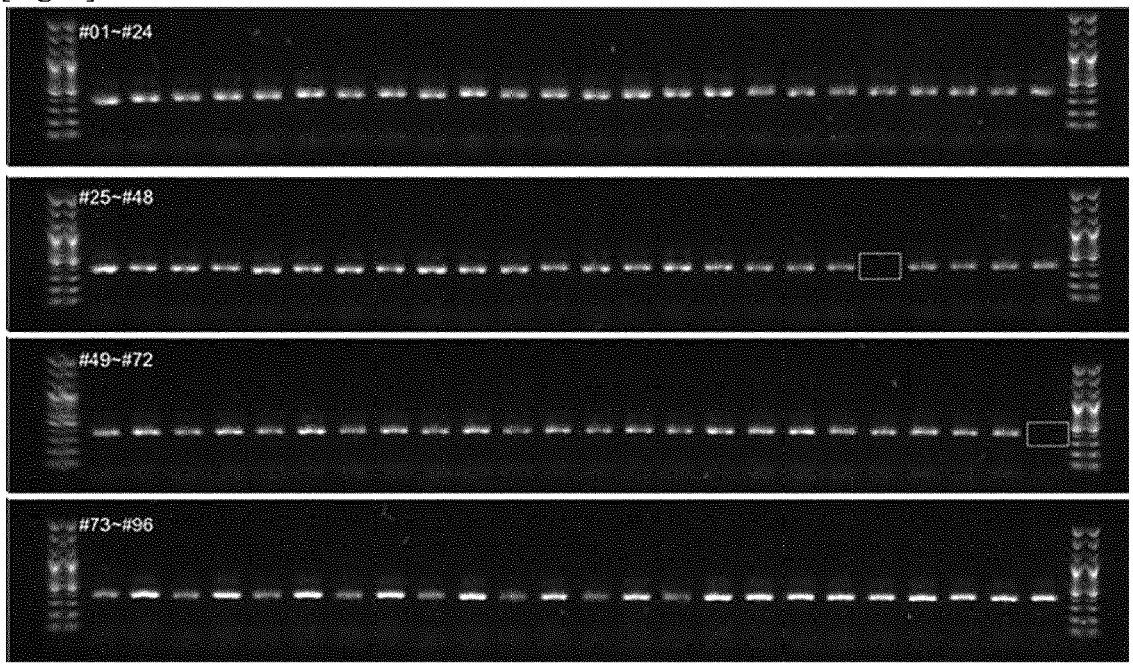

[Fig. 9]
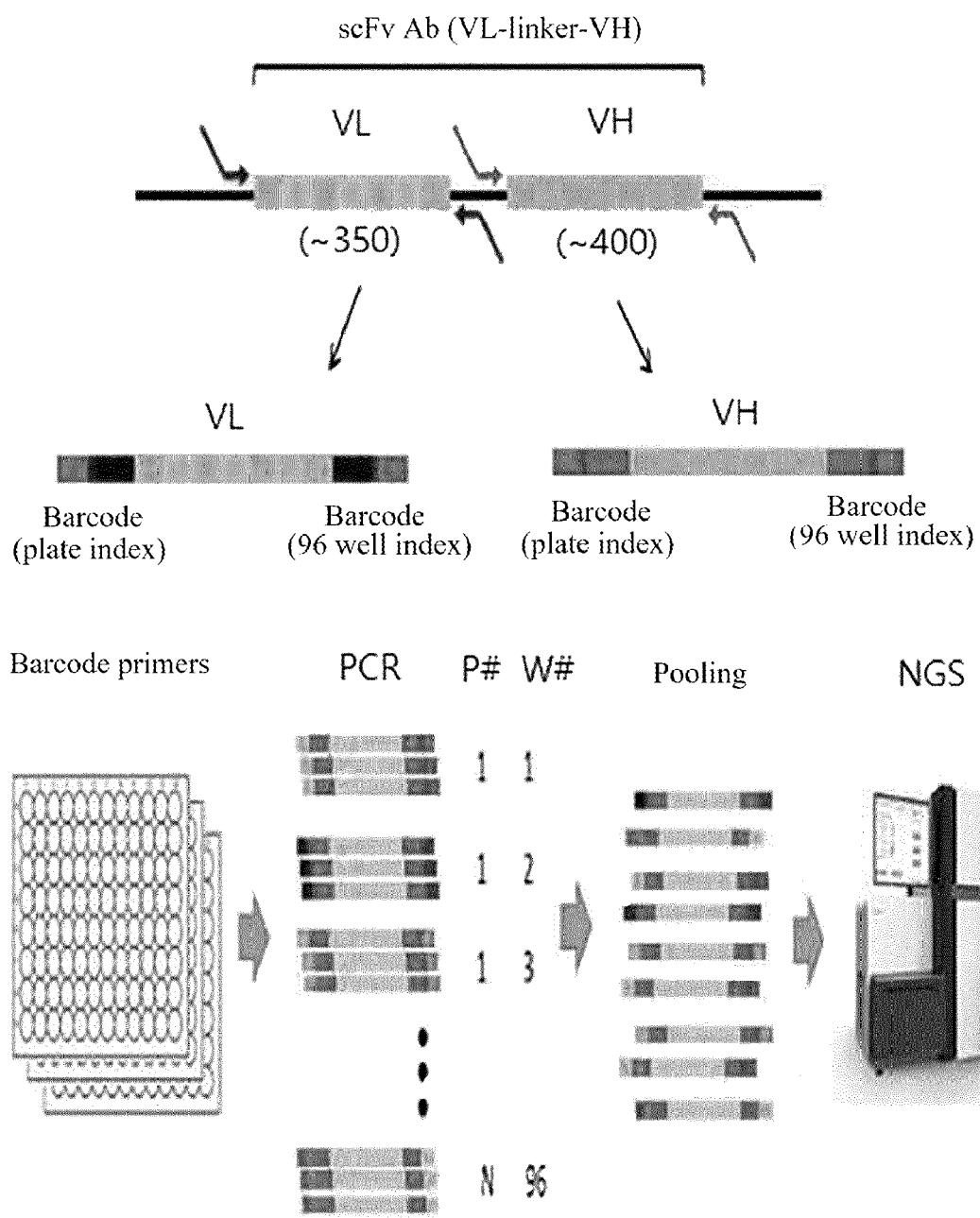

[Fig. 10]
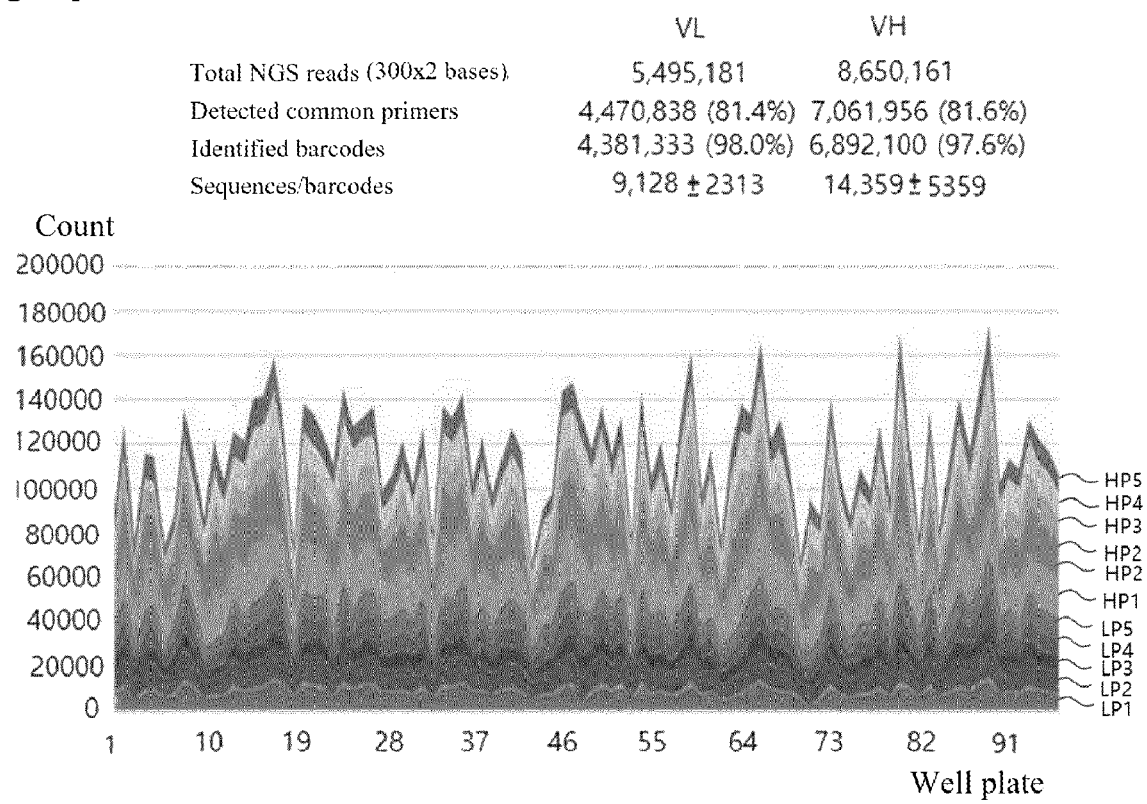

METHOD FOR SEPARATING, CAPTURING, ANALYZING AND RETRIEVING CELLS AND CELL PRODUCTS BY USING MICROSTRUCTURE

CROSS-REFERENCE TO RELATED APPLICATIONS

This application is the U.S. National Phase under 35 U.S.C. § 371 of International Application No. PCT/KR2018/005507 filed on May 14, 2018, which in turn claims the benefit of Korean Application No. KR 10-2017-0059325, filed on May 12, 2017, the disclosures of which are incorporated by reference into the present application.

TECHNICAL FIELD

The present invention relates to a technique for genomic library screening and provides a method for separating, capturing, analyzing, and retrieving cells and cell products by using a microstructure that can be preferentially applied to the field of antibody engineering for the development of new therapeutic antibodies and can be extensively applied to multiple genetic/phenotypic analysis of various biochemical molecules, for example, in the field of protein engineering and metabolic engineering.

BACKGROUND ART

Therapeutic antibodies are next-generation therapeutics that have more recently begun to receive attention due to their superior biostability and the resulting high pass rate in clinical trials and low development costs as well as their functionality as targeted therapeutics. A phage display technique enables human antibody library and synthetic antibody library screening in connection with the development of therapeutic antibodies and are widely used to not only develop new antibody therapeutics but also to discover antibodies satisfying various needs. In the utilization of the phage display technique, a reduction in time and cost required to analyze libraries for screening of relevant antibodies brings huge economic profits.

Antibody library screening is performed by sequencing individual DNA molecules constituting antibody libraries and analyzing the biochemical and physiological properties of antibody proteins corresponding to the sequences to obtain the DNA sequences of antibody proteins with desired properties. This process essentially involves various traditional molecular biological approaches, typified by cloning, using microorganisms such as E. coli. In connection with this, however, time and cost burdens required for analysis limit the scalability of screening, resulting in difficulty in discovering high quality antibodies.

Generally, antibody library screening consists of a process for reducing the size of an analyte library while reducing the number of potential candidates as optimal antibodies and a process for sequencing individual DNAs constituting the target library and analyzing the biochemical and physiological properties of the antibodies.

In the process for reducing the size of the library, a virus library containing DNA molecules is constructed using a phage display technique. Antibody proteins determined by the corresponding DNA sequences are expressed on the surface of the virus library. Interaction of the virus library with antigens binding to antibodies is induced to screen portions of the analyte library based on antigen specificity, which is considered a primarily important feature of antibodies. When the analyte antibodies are screened by the reaction of the antigens with the library, a small number of optimal antibodies may be excluded by competitive reactions with a large number of other non-optimal antibodies and may not be screened in the subsequent selection process, implying the possibility of loss of relevant optimal antibodies. In addition, the preparation of the library for screening involves amplification of DNAs or viruses with microorganisms. During this amplification, there is a possibility that the distribution of the antibodies in the library might be greatly altered. That is, genetic differences of the individual microorganisms or specificity of the antibodies produced causes large differences in the proliferation rate of the microorganisms and the production rate of the antibodies constituting the library, causing an alteration in the distribution of the library.

Constituent antibodies of an antibody library obtained from biological immune reaction products have the ability to bind to antigen molecules as targets for antibody discovery, but some of them do not have the ability to neutralize pathogenic antigens. Some antigens such as high-risk viruses known to be resistant to immune responses may have an epitope distribution in which a smaller number of major target epitopes associated with in vivo mechanisms and pathogenicity of the antigens are surrounded by a larger number of non-targeted epitopes and only some of them are exposed. As a result of immune responses to the antigens having an asymmetric epitope distribution, antibodies binding to the larger number of non-targeted epitopes are exclusively produced but most of them do not bind to major target epitopes, failing to have the ability to neutralize pathogenic antigens. That is, most of the antibodies produced are unnecessary. The unnecessary antibodies pass the library screening process but are obstacles to the discovery of relevant antibodies associated with the discovery of new drug candidates. Furthermore, the asymmetry of the relative distribution of relevant antibodies and unnecessary antibodies may be further increased after library amplification for biopanning.

The process for sequencing individual DNAs constituting the library and characterizing the antibodies includes cloning the analyte library to culture colonies of the individual DNA molecules constituting the library on a solid medium, separating the colonies to produce antibodies and analyzing various biochemical and physiological properties of the antibodies produced, including affinity for antigens, by a suitable assay such as enzyme-linked immunosorbent assay (ELISA), and sequencing the colonies by a suitable sequencing technique such as Sanger sequencing. This conventional method is very labor intensive and has problems in that the number of practically analyzable colonies is very limited compared to the scale of an analyte library and time and cost burdens required for analysis increase in proportion to the number of analyzable colonies.

In this connection, as the prior art, U.S. Patent Publication No. 2013-0190206 discloses a method for separating and culturing library-carrying single cells in spatially isolated microreaction chambers. This method has disadvantages in that a system and a process for collecting liquid staying on microcapillaries are complicated and there is an increased risk of cross-contamination of samples after collection.

DETAILED DESCRIPTION OF THE INVENTION

Problems to be Solved by the Invention

Thus, the present invention proposes a biochip designed for parallel analysis of the sequences and biochemical and physiological properties of antibodies constituting an antibody library and a method of using the biochip. Specifically, the present invention provides a biochip technology that can replace cloning processes of traditional methods essential for library screening to produce a large number of clones of individual DNA molecules constituting a library and to analyze and extract the clones. Particularly, the present invention provides a method for maximizing the efficiency of library screening by analyzing a large-scale library on a single molecular clone basis, such as phenotypic analysis of antibodies, and selectively separating the clones based on the analytical results. The present invention also provides an effective method for discovering relevant antibodies associated with the discovery of new drug candidates among antibodies that are exclusively produced as a result of immune responses to antigens having an asymmetric epitope distribution and bind to a large number of non-targeted epitopes.

Means for Solving the Problems

The present invention provides a technique for inducing cell growth and colony formation by dividing and arranging library-carrying cells in a number of microreaction chambers formed by assembly of chips having a microstructured array such as a microwell and culturing the spatially isolated cells. Specifically, the present invention provides a structure in which library-carrying cells and library-carrying products (secretions) produced by the cells are isolated in a number of microreaction chambers formed by assembly of a microstructured chip and a substrate and spatially isolated from one another and are captured on the capture surfaces of the microstructured chip and the substrate surrounding the microreaction chambers or in which when the chambers are hydrogelled, the materials contained in the chambers are confined in the hydrogels on the microstructure and the substrate.

Effects of the Invention

The technique of the present invention can be utilized for cell-mediated separation and amplification of individual DNA molecules constituting a DNA library. The technique of the present invention is also applicable to various fields of library screening for analyzing various phenotypic changes resulting from different sequences of DNA molecules in a DNA library. For example, the technique of the present invention may be utilized to find optimal conditions for microbial mutation in the field of metabolic engineering to investigate optimal microbial genetic transformation for biofuel production in maximum yields. Particularly, when very few relevant target molecules are present in a large-scale library, as in screening in the field of antibody engineering, the technique of the present invention provides an independent assay without being affected by other analyte molecules that can be utilized to discover trace molecules, which are difficult to find by general approaches. In addition, biological reaction products separated by the technique of the present invention can be effectively used to find significant antibodies by comparison with products obtained by existing antibody screening methods including cloning using microorganisms or products obtained by library analysis techniques such as next-generation sequencing.

BRIEF DESCRIPTION OF THE DRAWINGS

FIG. 1 is a conceptual schematic diagram illustrating the formation of an array of single-cell colonies and single-cell products including DNA libraries using microreaction chambers formed by a microwell and selective separation of the array, where specific or non-specific capture is enabled.

FIG. 2 is a process flow diagram illustrating the growth of cells and/or cell products (secretions) in microreaction chambers formed by a microwell and non-specific capture and separation of the cells and/or cell products (secretions) on the surfaces of the microreaction chambers by liquid drying, lyophilization or sample-surface interaction in the microreaction chambers.

FIG. 3 shows an array structure of individually separable hydrogel blocks whose size, shape, and arrangement are determined by a microstructured chip and a process flow diagram illustrating an application example of a biological sample array chip using the structure.

FIG. 4 shows microbial cells grown after isolation by a microwell and fluorescently labeled phage virus molecules captured on the capture surfaces of the microwell.

FIG. 5 shows hydrogelation of single-cell colonies using the microwell shown in FIG. 2.

FIG. 6 shows evaporation of an energy-absorbing layer and separation of a target-capture layer by irradiation of a pulsed laser onto a capture surface on which the cells and the cell products shown in FIG. 1 and FIG. 2 were captured and images of the target-capture layer separated into different shapes depending on the laser power.

FIG. 7 shows images of the single-cell colony hydrogels formed in FIG. 5 before and after evaporation of the energy-absorbing layer by irradiation of a pulsed laser onto the hydrogels and selective separation of the hydrogels.

FIG. 8 shows the results of screening conducted by the methods of FIGS. 1, 4, and 6.

FIG. 9 shows the entire scFv sequences of all samples obtained by NGS after barcoded PCR of the VH and VL regions of single chain variable fragments (scFvs) shown in FIG. 1 and barcoding based on the barcode data.

FIG. 10 shows barcode data obtained by NGS to capture the entire scFv sequences of all barcoded samples after barcoded PCR of the VH and VL regions of single chain variable fragments (scFvs) in FIGS. 1 and 9.

BEST MODE FOR CARRYING OUT THE INVENTION

The present invention proposes a technique for inducing cell growth and colony formation by dividing and arranging library-carrying cells in a number of microreaction chambers formed by assembly of chips having a microstructured array such as a microwell and culturing the spatially isolated cells. Specifically, the present invention provides a structure in which library-carrying cells and library-carrying products (secretions) produced by the cells are isolated in a number of microreaction chambers formed by assembly of a microstructured chip and a substrate and spatially isolated from one another and are captured on the capture surfaces of the microstructured chip and the substrate surrounding the microreaction chambers. The present invention also provides a structure in which different library-carrying cells and library-carrying products are confined in hydrogel blocks formed by gelling of the microreaction chambers. The reaction products captured on the microstructured chip and the substrate are exposed to the outside after chip detachment and can be used for sample analyses such as reactivity and affinity analysis or can be collected by contactless separation.

Particularly, the present invention utilizes the structural properties of the microstructure, in which individual cells are contained in a number of isolated parallel microreaction chambers, to analyze various types of samples and to separate the samples in either a contact or non-contact manner.

Embodiments of the present invention will now be described in detail with reference to the accompanying drawings. These embodiments are provided so that this disclosure will be thorough and complete, and will fully convey the scope of the invention to those skilled in the art. Accordingly, the present invention may be embodied in many different forms and should not be construed as limited to the exemplary embodiments set forth herein. In the drawings, the dimensions, such as widths, lengths, and thicknesses, of elements may be exaggerated for clarity. The drawings are explained from an observer's point of view. It will be understood that when an element is referred to as being "on" another element, it can be directly on the other element, or one or more intervening elements may also be present therebetween.

Specifically, the present invention provides a structure in which library-carrying cells and library-carrying products (secretions) produced by the cells are isolated in a number of microreaction chambers formed by assembly of a microstructured chip and a substrate and spatially isolated from one another and are captured on the capture surfaces of the microstructured chip and the substrate surrounding the microreaction chambers or are prepared in the form of hydrogels containing the constructs.

The term "library-carrying cells" as used herein refers to cells that have library information including DNA, RNA, etc. in the form of genomic DNA, plasmid, etc. and is not limited thereto. In addition, the cells can be interpreted as having a meaning that includes intracellular constructs and intracellular products released from cells as a result of mechanisms such as apoptosis or cell membrane disruption.

The term "library-carrying products" as used herein refers to a variety of types of products that can be obtained from vital activities of proteins (for example, antibodies and enzymes) expressed by library information, virus molecules including sequences of libraries in the form of DNA, RNA or display proteins, and cells (e.g., liposomes) including one or more of the products, but is not limited thereto.

For ease of description, the microstructured chip and the substrate are distinguished from each other. However, the microstructured chip and the substrate are not limited as long as they can be assembled to each other to form spatially isolated microreaction chambers and can perform either or both of their roles. The microstructured chip and the substrate are typically in the form of solids or hydrogels, for example, glass, silicon, polydimethylsiloxane (PDMS), agarose, and alginate.

The microreaction chambers should be able to maintain their state such that the isolated library-carrying cells and the isolated library-carrying products (secretions) produced by the cells are not mixed even in subsequent processes, including a state in which the isolated library-carrying cells and/or the isolated library-carrying products (secretions) produced by the cells are immobilized or their motion is retarded. Specifically, the microreaction chambers mean spaces surrounded by the surfaces of a solid, generally glass or silicon. Herein, in a broader concept, the microreaction chambers will be used as spaces surrounded by the surfaces of a gel-state material, such as polyacrylamide, agarose or alginate, or the surfaces of a liquid such as water, ethanol or oil. This concept is subdivided into: solid substrates, for example, a substrate replicated from a template, a substrate accommodating an energy-absorbing layer, a substrate coated with a sacrificial layer on a surface of the substrate, a substrate undergoing a phase transition by an electromagnetic field, and a transparent or opaque solid substrate including a combination thereof, and substrates whose surfaces are modified such that the isolated library-carrying cells or the isolated library-carrying products (secretions) produced by the cells can be captured.

The isolated library-carrying cells or the isolated library-carrying products (secretions) produced by the cells may be located on the surfaces of the corresponding microreaction chambers by specific and/or non-specific intermolecular binding based on affinity or physical or chemical intermolecular interaction such as adsorption. Alternatively, the isolated library-carrying cells or the isolated library-carrying products (secretions) produced by the cells may be contained in hydrogels formed on the microstructured chip or the substrate by hydration of the microreaction chambers and may be located on the substrate. The library-carrying cells or the library-carrying products (secretions) produced by the cells are isolated by the microstructured chip and are located randomly. However, the microreaction chambers may be spaced at intervals of at least 1 μm from one another, which ensures easier subsequent extraction. The intervals may be from 100 nm to 1 cm, preferably from 1 μm to 1 mm, more preferably from 10 μm to 500 μm.

The cells are intended to embrace those derived from biological samples having biological functions, for example, genetic materials such as DNA, peptides, proteins, microorganisms, viruses, plant cells, animal cells, and carriers containing them. Specifically, the biological samples may be selected from the group consisting of: genetic materials such as deoxyribonucleic acid (DNA), ribonucleic acid (RNA), locked nucleic acid (LNA), peptide nucleic acid (PNA), threose nucleic acid (TNA), glycol nucleic acid (GNA), xeno nucleic acid (XNA), synthetic nucleic acid, and modified nucleic acid; proteins; cells such as viruses, prokaryotic cells, eukaryotic cells; and carriers containing them.

The microreaction chambers may be made of a material that supplies nutrients for vital activities of cells to create an environment for vital activities of cells, such as cell growth and protein expression, etc. Alternatively, a curable material in the form of a liquid or gel or a vaporizable or sublimable material may be used for the microreaction chambers.

The extraction process includes contact extraction and non-contact extraction. A disposable or reusable pipette tip, a glass microtube or a metal material may be used for contact extraction. The non-contact extraction may be performed with the application of ultrasonic waves, a pneumatic pressure or a laser. For high-yield economic extraction of the isolated library-carrying cells and/or the isolated library-carrying products (secretions) produced by the cells, non-contact extraction is more preferred than contact extraction using a disposable tool or a tool that needs to be washed after use. For easy non-contact extraction, the sizes of the capture surfaces from which the cells and the cell products are separated and collected are 500 μm or less in every direction. The library-carrying cells and/or the library-carrying products (secretions) produced by the cells separated by non-contact extraction are collected in an underlying reservoir. The reservoir may be empty or contain various materials in the form of liquids or gels for stable collection or disruption and DNA amplification of the extracted isolated library-carrying cells and/or the extracted library-carrying products (secretions) produced by the cells in subsequent processes. The reservoir has a size of 10 μm to 10 cm, preferably 100 μm to 1 cm, which is advantageous for easy collection. Commercially available products of the reservoir include Petri dishes, 96-well plates, and 384-well plates. A container structure based on a microstructure such as a microwell designed for mass production is also suitable as the reservoir for collection and storage.

According to one embodiment of the present invention, the biological sample chip may have a structure in which library-carrying cells' and library-carrying reaction products' produced by the cells are isolated in a number of microreaction chambers formed by assembly of a microstructured chip and a substrate and spatially isolated from one another and are captured on the capture surfaces of the microstructured chip and the substrate surrounding the microreaction chambers or are contained in hydrogels formed on the surfaces wherein the reaction products captured on the microstructured chip and the substrate are exposed to the outside after chip detachment and can be used for sample analyses such as reactivity and affinity analysis or can be collected in contactless separation.

According to one embodiment of the present invention, the biological sample chip may include a structure as a reference mark on the microstructured chip and/or the substrate in order to efficiently recognize an accurate positional relationship of the array of biological samples formed on the microstructured chip and the substrate.

According to one embodiment of the present invention, a method for capturing a number of library-carrying cells and library-carrying biological reaction products produced by the cells on the surfaces of the microstructured chip and the substrate using the microstructured chip may be carried out in the following order: i) a solution including library-carrying cells is spatially dispensed in microreaction chambers using the microstructured chip and the counterpart substrate; ii) products of biological reactions (such as growth of the cells and secretion from the cells) in the microreaction chambers are captured on the microstructured chip and the substrate; and iii) the microstructured chip and the substrate are detached from each other to provide the library-carrying biological reaction products in forms that are easy to use for analysis and sample collection in subsequent processes.

According to one embodiment of the present invention, there is provided a method for preparing a biological sample analysis chip which includes spatially dividing, isolating, and arranging samples including library-carrying cells and performing biochemical reactions of the cells wherein the samples are isolated and arranged such that cell products produced by the biochemical reactions and the cells are captured using a number of closed reaction chambers formed by assembly of a microstructure and a substrate or some or all of the surfaces surrounding the reaction chambers.

For example, the substrate may be selected from a second microstructure different from the microstructure, a flat plate, a film, a net-shaped flat plate or film through which the samples can selectively pass based on its size and chemical properties, and combinations thereof, which are preferable in that various forms of closed reaction chambers can be provided if needed. The second microstructure may have a structure or arrangement identical or similar to the microstructure to expand the reaction chambers. Alternatively, the second microstructure may be a microstructure protruding to fill portions of the reaction chambers. Alternatively, the second microstructure may have a larger size than the microstructure such that the two microstructures form one reaction chamber. Alternatively, the second microstructure may consist of ultrafine structures (for example, patterned nanostructures) having smaller sizes than the microstructure and accommodated in each reaction chamber. However, there is no restriction on the structure of the second microstructure.

The biochemical reactions may be performed using a biochemical liquid preparation under conditions for growing the cells, for inducing apoptosis or cell membrane disruption or for secreting the cell products such as virus molecules. Examples of suitable biochemical liquid preparations include, but are not limited to, buffers creating conditions for physiological activities of the cells, media supplemented with nutrients for growth and differentiation of the cells, and solutions containing active materials for maximizing specific signal system stimulation and specific activity of the cells.

Specifically, the cell products produced by the biochemical reactions and the cells may be captured on the surface(s) of the microstructure and/or the surface of the substrate surrounding the samples and the reaction chambers based on the principle of adsorption or binding by intermolecular binding or sample-surface interaction, for example van der Waals forces, hydrophobic interaction, electrostatic force or affinity.

FIG. 1 is a conceptual schematic diagram illustrating the formation of an array of single-cell colonies and single-cell products including DNA libraries using microreaction chambers formed by a microwell and selective separation of the array, where specific or non-specific capture is enabled. According to the technique of the present invention, isolated library-carrying cells and isolated library-carrying products (secretions) produced by the cells may be located on or in a solid substrate, a gel, a curable material, and a liquid that can form spaces. For ease of explanation, FIG. 1 illustrates a state in which isolated library-carrying cells and isolated library-carrying products (secretions) produced by the cells are located on the surfaces of a microstructured chip and a solid substrate. Referring to FIG. 1, the concentration of cells is adjusted such that only single cells are contained in the corresponding microreaction chambers formed by the microstructure formed on a chip. This concentration adjustment enables the creation of conditions for culture and growth of the cells without competing with other cells. Since the cell products produced by the cells under the single-cell culture conditions are exposed to the same capture surfaces under the same environment, their capture on the capture surfaces is determined without interfering or competing with other cells and cell products. This feature essentially enables the discovery of optimal antibodies based on affinity for specific materials (including antigens) constituting the target-capture surfaces. In addition, the target-capture surfaces are designed to have a common physical/chemical affinity for the cells or the cell products (secretions) irrespective of library information and the cells or the cell products provided in the microreaction chambers formed on the chip are collectively captured in a specific or non-specific manner and can be used for affinity analysis and selective separation in subsequent steps.

The cells and the cell products are amplified and captured in amounts at similar levels without using specific materials (including antigens above described), that is, in a non-specific manner. In addition, the parallel arrangement of the microreaction chambers having small volumes can lead to time and cost savings and is effective in greatly increasing the number of analyzable molecules and the size of libraries, unlike in the prior art.

In the utilization of the chip after separation, the assembly of the microstructured array and the substrate as two elements of the chip enables capture of the samples (including the cells and the cell products produced by the cells) on the capture surfaces or provides the samples in the form of hydrogel blocks in the microreaction chambers. The capture surfaces and the hydrogel blocks can be retrieved by various energy applications to individually retrieve the cells and the cell products from their array. Depending on their type, the cells and cell products can be retrieved after various amplification processes such as cell culture, viral infection, and DNA amplification such as polymerase chain reaction (PCR). Suitable amplification processes using polymerase include, but are not limited to, polymerase chain reaction (PCR), in vitro transcription, reverse transcription, linear amplification, multiple displacement amplification (MDA), rolling circle amplification (RCA), emulsion PCR, emulsion PCR using beads, bridge PCR, intracellular infusion, intracellular cloning, and combinations thereof.

The cells are not limited to a particular type as long as they can divide. The cells are mammalian cells as well as microbial cells, such as *E. coli* or yeast cells. The use of rapidly dividing microbial cells is advantageous for the amplification of nucleic acid molecules except for special cases.

The special purposes include when proteins such as antibodies are expressed intracellularly, specific genes are expressed, gene cloning is impossible in specific cells, host cells are infected with bacteriophages or viruses, and enzymes such as restriction enzymes or transposable elements affecting specific sequences are present in cells.

Another possibility of utilizing the separated chip is to provide analysis of the captured cell products, such as affinity quantification. For example, when it intends to search for antibodies on the sample capture surfaces, the surfaces are treated with molecules including specific epitopes of antigen materials or antigens to selectively select different antibody molecules produced by the cells in the microreaction chambers and the antibody molecules are labeled with a fluorescently labeled antibody having a common affinity therefor to collectively determine the antigen specificities of the antibody molecules produced by the cells provided on the chip. Therefore, the technique of the present invention can easily replace the prior art that requires much cost and labor. In addition, since the antibody molecules are captured on the surfaces of the chip and the substrate or in the hydrogel blocks without being affected by interaction with other antibody molecules, affinity analysis can be performed without the need to consider competitive reactivities, enabling analysis of affinities for a relatively small number of distributed antibody molecules. The obtained analytical results for antigen specificity can also be used as reference marks in the sample collection process.

FIG. 1 is an exemplary conceptual schematic diagram illustrating the assembly of a microstructured array and a counterpart substrate. The two elements are distinguished in terms of their function for illustration of the drawing and are not limited as long as they can be assembled to each other to form microreaction chambers while performing either or both of their roles. For example, one substrate may be used to analyze the products and the other substrate may be used to collect the products. Alternatively, only one substrate may be used to analyze and collect the products. In addition, A target-capture layer or its surface treated with a different material may be formed to easily induce specific or non-specific capture of the samples during collection or reduce possible damage to the captured samples during collection. An additional energy-absorbing layer may be formed to easily separate and collect the captured samples in a non-contact manner.

According to the present invention, since the samples can be directly adsorbed or bound onto a base, the target-capture layer does not necessarily have to be formed. If necessary, the target-capture layer may be formed on a base of the substrate. The target-capture layer is provided on the surface of the base to increase or decrease the surface capture efficiency of the samples. The target-capture layer may be provided for the purpose of substituting or modifying the surface characteristics of the microstructure or the substrate such that biochemical molecular materials having a molecular selectivity for ligand, antibody and the like or various biochemical molecular materials such as hydrophilic/hydrophobic/amphiphilic materials providing selectivity associated with hydrophilicity/hydrophobicity are easily provided on the surfaces. Alternatively, the surface treating materials may be contained in a polymer or hydrogel matrix and deposited on the surfaces.

An energy-absorbing layer may be optionally further formed on the base of microstructure or the substrate. The energy-absorbing layer has the ability to absorb energy applied externally from the microstructure or the substrate. Due to this ability, the energy-absorbing layer can convert the absorbed energy into a different form of energy that can be utilized to separate the target samples from the microstructure or the substrate by a phenomenon such as phase transition when the samples are separated in a non-contact manner, for example, by the application of pulsed laser energy. Preferably, the energy-absorbing layer maximizes the energy conversion efficiency depending on the type and feature of the externally applied energy to protect the samples. The energy conversion efficiency can be adjusted for a variety of purposes such as sample disruption. When the energy-absorbing layer is provided together with the target-capture layer, the energy conversion efficiency may be adjusted to conserve the target-capture layer and control the sample disruption. The energy-absorbing layer may be provided in the form of a metal oxide thin film on the microstructure or the substrate. Alternatively, the energy-absorbing layer may be formed by incorporating molecules or fine particles into a matrix material such as a polymer or hydrogel on the surfaces. However, there is no restriction on the form of the energy-absorbing layer. The energy-absorbing layer does not necessarily have to be provided when energy is directly applied to the samples or the target-capture layer to separate the samples.

Specifically, the cell products produced by biochemical reactions and the cells can be captured on the surfaces of the microstructure and/or the surface of the substrate surrounding the closed reaction chambers based on the principle of adsorption or binding by drying of the biochemical liquid preparation, lyophilization or sample-surface interaction.

FIG. 2 illustrates an embodiment of the biological sample chip of FIG. 1 and is a process flow diagram illustrating non-specific capture and separation of library-carrying cells and/or cell products (secretions) on the surfaces of microreaction chambers by drying, lyophilization or sample-surface interaction of an assembled biological sample chip. Referring to FIG. 2, the constituent biological samples of the array formed by the microstructure contain different library-carrying cells and/or different library-carrying products (secretions) produced by the cells.

According to an embodiment, a method for forming library-carrying cells or cell products that can be separated using the microstructured chip may be carried out in the following order: i) a solution containing library-carrying cells is spatially dispensed using a microstructured chip and a counterpart substrate; ii) biochemical reactions, including growth of the cells and secretion of virus molecules, are allowed to occur in the isolated reaction chambers; iii) non-specific adsorption of the cells and/or cell products (secretions) to the target-capture surfaces is induced through drying, lyophilization or sample-surface physicochemical interaction; and iv) the microstructure is detached from the substrate such that the array of the cells and the cell products is exposed for contactless separation.

The process flow diagram of FIG. 2 can be used in conjunction or combination with the capture of cells or cell products (secretions) using capture surfaces according to the embodiment illustrated in FIG. 1. Specific and non-specific capture based on intermolecular affinity and non-specific capture based on molecular adsorption may be the same as or different from each other depending on the preparation of the capture surfaces of the microstructured array chip and the substrate. For ease of capture of the samples and selective separation and collection of the captured samples, a target-capture layer or an energy-absorbing layer may be further formed on the microstructured chip or the substrate.

According to a further embodiment, the biological sample chip may have a structure in which library-carrying cells and/or cell secretions as biological samples are contained in an individually separable hydrogel block array structure and individual hydrogel blocks whose size, shape, and arrangement are determined by the microstructured chip.

According to an embodiment, a method for forming separable library-carrying cell complex hydrogels using the microstructured chip may be carried out in the following order: i) a solution containing library-carrying cells is spatially dispensed using a microstructured chip and a counterpart substrate; ii) biochemical reactions are allowed to occur in isolated reaction chambers and the reaction chambers are gelled to form hydrogel blocks; and iii) the microstructure is detached from the substrate such that the hydrogel blocks are exposed for contactless separation.

If necessary, the microstructure or the substrate may include an adhesion controlling layer formed on the base. The adhesion controlling layer serves to easily provide the hydrogel blocks formed on the microstructure or the substrate. The adhesion controlling layer may be formed using a molecular material having a physicochemical affinity or the ability to bind to both the surfaces of the microstructure or the substrate and the hydrogel blocks. The molecular material may be coated on the surfaces of the microstructure or the substrate. Alternatively, a material having a physicochemical affinity or the ability to bind to the hydrogel blocks may be deposited on the microstructure or the substrate to form the adhesion controlling layer. Alternatively, a material identical or similar to the material for the hydrogels may be provided on the surfaces of the microstructure or the substrate, followed by gelling to form the adhesion controlling layer in the form of a hydrogel film on the surfaces of the microstructure or the surface of the substrate.

For the purpose of replacing the function of the adhesion controlling layer, a material having affinity for the microstructure or the substrate may be added to the hydrogel-forming material arranged in the reaction chambers for gelation of the reaction chambers so that an increase in the ability to bind to the surfaces is induced.

The above-described methods for forming the adhesion controlling layer may be used in combination but the adhesion controlling layer does not need to be provided if hydrogel blocks are easily formed on the surfaces.

If necessary, an energy-absorbing layer may be formed on a base of the microstructure or the substrate. The energy-absorbing layer has the ability to absorb energy applied externally from the microstructure or the substrate. Due to this ability, the energy-absorbing layer can convert the absorbed energy into a different form of energy that can be utilized to separate the target samples from the microstructure or the substrate by a phenomenon such as phase transition when the samples are separated in a non-contact manner, for example, by the application of pulsed laser energy. The energy-absorbing layer may be provided in the form of a metal oxide thin film on the surface of microstructure or the substrate. Alternatively, the energy-absorbing layer may be formed by incorporating molecules or fine particles into a matrix material such as a polymer or hydrogel on the surfaces. However, there is no restriction on the form of the energy-absorbing layer. The energy-absorbing layer does not necessarily have to be provided because the hydrogel blocks can be separated by direct application of energy.

After the isolation/arrangement and the biochemical reactions, the microstructure and the substrate forming the closed reaction chambers are detached from each other to provide an analysis chip set in which the same library-carrying cell products and/or cells are obtained on the microstructure or the substrate. The analysis chip set can be used to analyze the biochemical and physiological properties of the library constructs contained in the reaction chambers or the sequences of the library constructs and/or to selectively separate the captured samples.

Specifically, the isolation/arrangement and the biochemical reactions are performed by introducing a hydrogel-forming (hydrogelation) material into the reaction chambers then by gelling the material. The gelling of the hydrogel-forming material can lead to the formation of hydrogels on the surfaces of the microstructure or the surface of the substrate.

FIG. 3 shows an array structure of individually separable hydrogel blocks whose size, shape, and arrangement are determined by a microstructured chip according to the present invention, and a process flow diagram illustrating an application example of a biological sample array chip using the structure. Referring to FIG. 3, a number of hydrogel blocks formed by the microstructure include different library-carrying cells and different library-carrying cell products produced by the cells.

The process flow diagram of FIG. 3 can be used in conjunction or combination with the capture of cells or cell products using capture surfaces according to the embodiment illustrated in FIG. 1. The reactions (cell growth, material secretion, intermolecular interaction, etc.) in microreaction chambers formed by the microstructured chip and the gelation of the microreaction chambers may be carried out in the reverse order. The hydrogel block array may be left attached to the microstructured chip or may be transferred to another substrate. An adhesion controlling layer may also be formed on the microstructured chip or the substrate to determine the locations of the hydrogel blocks. For ease of separation of the hydrogel blocks, an energy-absorbing layer may be further formed on the microstructured chip or the substrate. The adhesion controlling layer may be formed via the energy-absorbing layer. The energy-absorbing layer and the adhesion controlling layer are the same as those described above and thus their description is omitted.

For example, the cells or the cell constructs present in the hydrogels formed on the surfaces of the microstructure or the substrate may be used to analyze the sequences, biochemical properties, and physiological properties of the library constructs or to selectively separate the captured samples.

According to another embodiment of the present invention, there is provided a biological sample analysis chip including a microstructure-based analysis chip and/or a substrate-based analysis chip obtained by the above-described method wherein library-carrying cells and/or library-carrying cell products formed by biochemical reactions of the cells are captured on the surfaces of one or both of the microstructure-based analysis chip and the substrate-based analysis chip or are captured in the form of hydrogel blocks. One of the microstructure-based analysis chip and the substrate-based analysis chip can be used to characterize the captured cell products and/or cells and to determine the locations of the captured cell products and/or cells and separate the captured cell products and/or cells for sample provision.

The same library-carrying cells and/or the same library-carrying cell products formed by biochemical reactions of the cells are captured on the surfaces of the microstructure-based analysis chip and the substrate-based analysis chip or are captured in the form of hydrogel blocks. One of the microstructure-based analysis chip and the substrate-based analysis chip can be used to characterize the captured cell products and/or cells and the other analysis chip can be used to determine the locations of the captured cell products and/or cells and separate the captured cell products and/or cells for sample provision.

The characterization can be performed by a suitable imaging method, including light field imaging, dark field imaging or fluorescence imaging, to provide information on whether the cells grow and/or fluorescently labeled molecules bind to the cells. The location determination enables analysis of information on the location of the cell products or the cells to be separated for sample provision by providing a reference mark on the microstructure-based analysis chip or the substrate-based analysis chip.

One of the analysis chips can be used to characterize the cell products and/or the cells, and the other analysis chip can be used to determine the locations of the same library-carrying cell products and/or the same library-carrying cells.

Location information of the microstructure or the reference mark in images of the analysis chips obtained before or after detachment of the analysis chips can be used to provide the locations of the same library-carrying cell products or the same library-carrying cells on the microstructure-based analysis chip and the substrate-based analysis chip.

The microstructure-based analysis chip and the substrate-based analysis chip can be used for antibody library screening or multiple genetic and/or phenotypic analysis of biochemical molecules.

According to another embodiment of the present invention, there is provided a method for separating biological samples, including: spatially dispensing a solution containing a number of library-carrying cells using a microstructure and a counterpart substrate to form microreaction chambers for the individual cells; confining the library-carrying cells and library-carrying cell products formed by growth and biochemical reactions of the cells in the microreaction chambers, linking binding ligands to two or more of the surfaces of the microstructure and the substrate surrounding the microreaction chambers, and inducing specific or non-specific interaction between the library-carrying cell products and the library-carrying cells in the individual microreaction chambers via the binding ligands; and detaching the microstructure and the substrate from each other to expose the library-carrying biological reaction products. For example, the binding ligands may physicochemically interact with one or more of the surfaces of the microstructure and the substrate. Desired ones of the library-carrying biological reaction products may be exposed by contact or non-contact extraction.

The method may further include creating conditions for determining changes in the optical properties of cell colonies grown from the cells in the microreaction chambers by imaging.

According to another embodiment of the present invention, there is provided a method for separating biological samples, including: i) adding cells to a gellable solution to prepare a cell suspension; ii) isolating and arranging the cell suspension in a number of microreaction chambers having uniform volumes using a microstructure formed on a chip; iii) gelling the solution to form solid microreaction chambers into which the cells are immobilized; and iv) growing the single cells confined in the solid microreaction chambers to create conditions for colony formation. The method may further include creating conditions for determining changes in the optical properties of cell colonies grown from the cells in the microreaction chambers before or after immobilization into the microreaction chambers by imaging, followed by detachment. Alternatively, the method may further include creating conditions for determining changes in the optical properties of cell colonies grown from the cells, which are associated with colonization, in the microreaction chambers before or after immobilization into the microreaction chambers by imaging after chip detachment.

According to another embodiment of the present invention, there is provided a method for separating biological samples, including i) adding cells to a gellable solution to prepare a cell suspension; ii) isolating and arranging the cell suspension in a number of microreaction chambers having uniform volumes using a microstructure formed on a chip; iii) growing the single cells confined in the microreaction chambers to create conditions for colony formation; and iv) gelling the solution to form solid microreaction chambers into which the cell colonies are immobilized. The method may further include creating conditions for determining changes in the optical properties of cell colonies grown from the cells in the microreaction chambers before or after immobilization into the microreaction chambers by imaging, followed by detachment. Alternatively, the method may further include creating conditions for determining changes in the optical properties of cell colonies grown from the cells, which are associated with colonization, in the microreaction chambers before or after immobilization into the microreaction chambers by imaging after chip detachment.

Under the imaging conditions, the formation of colonies of growing small-sized cells such as prokaryotic cells (e.g., bacterial cells) in the reaction chambers can be induced and observed even at an optical magnification as low as 5× to 100× where single cells are not easy to image. The solid microreaction chambers may be obtained in the form of hydrogels by introducing a hydrogel-forming material into the microreaction chambers and gelling the hydrogel-forming material.

According to another embodiment of the present invention, there is provided a method for library screening using library-carrying biological reaction products wherein the library-carrying biological reaction products are separated and analyzed by spatially dispensing a solution containing a number of library-carrying cells using a microstructure and a counterpart substrate to form microreaction chambers where the cells are isolated and arranged, inducing biochemical reactions of the cells in the microreaction chambers to produce library-carrying cell constructs or cells, allowing the library-carrying cell constructs produced by the biochemical reactions of the cells or cells to interact with one another on the surfaces of the microstructure and the substrate surrounding the microreaction chambers, and detaching the microstructure and the substrate from each other to expose the library-carrying biological reaction products.

According to another embodiment of the present invention, there is provided a method for library screening using library-carrying biological reaction products wherein the library-carrying biological reaction products are separated and analyzed by spatially dispensing a solution containing a number of library-carrying cells using a microstructure and a counterpart substrate to form microreaction chambers where the cells are isolated and arranged, inducing biochemical reactions of the cells in the microreaction chambers to produce library-carrying cell constructs by the biochemical reactions of the cells or cells, linking binding ligands to one or more of the surfaces of the microstructure and the substrate surrounding the microreaction chambers, allowing the library-carrying cell constructs produced by the biochemical reactions of the cells or cells to interact with the surfaces via the binding ligands, and detaching the microstructure and the substrate to expose the library-carrying biological reaction products.

According to another embodiment of the present invention, there is provided a method for library screening using library-carrying biological reaction products wherein the library-carrying biological reaction products are separated by adding cells to a gellable solution to prepare a cell suspension, isolating and arranging the cell suspension in a number of microreaction chambers having uniform volumes using a microstructure formed on a chip, growing the single cells confined in the limited microreaction chambers to create conditions for colony formation, gelling the solution to form solid microreaction chambers into which the cells are immobilized, and observing cell colonies under imaging conditions. The solid microreaction chambers may be obtained by solidifying hydrogels. Desired ones of the library-carrying biological reaction products may be separated by contact or non-contact extraction. The separated biological reaction products may be single chain variable fragments (ScFvs) carrying antibody information in the form of vL-linker-vH. In this case, the method may further include barcoding the DNAs of the biological reaction products, followed by parallel sequencing. The separated biological reaction products are applied to multiple genetic/phenotypic analysis of biochemical molecules for antibody library screening.

According to another embodiment of the present invention, there is provided a method for library screening using library-carrying biological reaction products wherein the library-carrying biological reaction products are separated by adding cells to a gellable solution to prepare a cell suspension, isolating and arranging the cell suspension in a number of microreaction chambers having uniform volumes using a microstructure formed on a chip, gelling the solution to form solid microreaction chambers in which the cells grow, allowing the grown single cells to form colonies confined in the limited microreaction chambers, and observing the cell colonies under imaging conditions. The solid microreaction chambers may be obtained by solidifying hydrogels. Desired ones of the library-carrying biological reaction products may be separated by contact or non-contact extraction. The separated biological reaction products may be single chain variable fragments (ScFvs) carrying antibody information in the form of vL-linker-vH. In this case, the method may further include barcoding the DNAs of the biological reaction products, followed by parallel sequencing. The separated biological reaction products are applied to multiple genetic/phenotypic analysis of biochemical molecules for antibody library screening.

Biological reaction products separated by the present invention can be effectively used to find significant antibodies by comparison with products obtained by existing antibody screening methods including cloning using microorganisms or products obtained by library analysis techniques such as next-generation sequencing.

MODE FOR CARRYING OUT THE INVENTION

Hereinafter, the present invention will be described in more detail.

1. Growth of Microbial Cells to Imageable Level after Isolation by Microwell and Fluorescent Labeling of Phage Virus Molecules Produced from Captured Cells on Capture Surfaces of the Microwell FIG. 4 shows microbial cells grown to an imageable level after isolation by the microwell of FIG. 1 and fluorescently labeled phage virus molecules produced by the cells captured on the capture surfaces of the microwell. Specifically, ER2738 strain cells were used as the microbial cells and a scFv library was biopanned four times with the pComb3 vector. The fluorescent labeling was performed by reaction with a FITC-conjugated anti-M13 mouse antibody at a concentration of 1 μg/ml. In FIG. 4, the red arrows indicate microreaction chambers where cells were grown and antigen-specific phage virus molecules were captured and detected on the corresponding capture surfaces, and the black arrows indicate microreaction chambers where cells were grown but antigen-specific phage virus molecules were not detected on the corresponding capture surfaces.

2. Formation of Single-Cell Colony Hydrogels Using Microwell

FIG. 5 shows hydrogelation of single-cell colonies using the microwell shown in FIG. 2. Specifically, ER2738 strain cells were cultured in SuperBroth to produce single-cell colonies. Hydrogels were formed using the culture broth in 1% low-melting agarose. Referring to FIG. 5, cells were grown in microreaction chambers formed by assembly of the microstructured chip and the substrate, and the chip and the substrate were detached from each other after hydrogel formation. A hydrogel block array was formed on the substrate in a state in which the grown cells and virus molecules produced by the cells were confined by the cured hydrogel blocks. The locations of the hydrogel blocks formed by physical and chemical surface treatment of the microstructured chip, the substrate, and the hydrogels can be determined as desired inside the flat substrate or the microstructured chip.

3. Separation of Target-Capture Layer by Evaporation of Energy-Absorbing Layer with Pulsed Laser Irradiation FIG. 6 shows the separation of a target-capture layer by evaporating an energy-absorbing layer with pulsed laser irradiation. Specifically, when a pulsed laser was irradiated onto the vicinity of samples in a structure in which ITO (Indium-Tin-Oxide) as an energy-absorbing layer and PDMS as a target-capture layer were formed on a glass substrate from the top to the bottom, the target-capture layer was disrupted and transferred to a reservoir at a high laser power (see the left of FIG. 6) but the target-capture layer was transferred to a reservoir while a portion thereof remained intact at a low laser power (see the right of FIG. 6). A microwell structure having dimensions of 250 μm (width× length×height) was used as the reservoir. A microwell structure having different dimensions, a 96-well plate or a 384-well plate may also be used as the reservoir.

The energy-absorbing layer may be made of a light-transmitting metal oxide or a light-transmitting plastic material. For example, the energy-absorbing layer may be made of glass or silicon whose transmittance is reduced or whose absorbance is increased to increase energy absorption. Alternatively, the energy-absorbing layer may be surface-coated glass or silicon. The energy-absorbing layer may be interposed between two or more different layers such as the substrate and the target-capture layer. Alternatively, the energy-absorbing layer may be present in a solid such as glass or silicon. However, the location of the energy-absorbing layer is not particularly limited. The energy-absorbing layer is preferably made of a material free of optical distortion such that it is easy to determine whether laser light is accurately applied to the target samples.

When the target samples are biological materials such as cells, the pulsed laser may be a laser that uses light energy in the infrared wavelength region to reduce damage to the target samples. In this case, it is preferred that the energy-absorbing layer is evaporated by an infrared laser and transmits visible light to avoid interference with imaging of the biological materials. The energy-absorbing layer is preferably formed using a metal oxide. The metal oxide may be, for example, indium tin oxide (ITO), indium zinc oxide (IZO), zinc oxide (ZnO), indium zinc tin oxide (IZTO), cadmium tin oxide (CTO) or indium gallium zinc oxide (IGZO) but is not limited thereto.

It is preferred that the energy is directly applied to the energy-absorbing layer to prevent damage to the target samples. For example, the energy has a density sufficient to evaporate sites of the energy-absorbing layer where the target samples are located. When the sites of the energy-absorbing layer to which the energy is applied are completely evaporated, the target samples are detached from the substrate. Accordingly, it is preferred that only the upper portion of the energy-absorbing layer to which the energy source is applied is partially evaporated without the need to completely evaporate the energy-absorbing layer where the target samples are located and the target samples are detached from the substrate in a state in which the target samples are located on the remaining portions of the energy-absorbing layer. An additional target-capture layer may be interposed between the target samples and the energy-absorbing layer to protect the target samples from various causes of damage such as thermal energy and vibrational energy caused by evaporation of the energy-absorbing layer. The applied energy may be in the infrared, visible or ultraviolet wavelength region and the energy source may be a pulsed laser. A pulsed laser useful as the energy source may have a wavelength of 10 to 10,000 nm, preferably 20 to 5,000 nm, more preferably 100 to 2,000 nm. Since most commercial pulsed lasers operate in the wavelength range described above, the system is easy to implement.

The pulsed laser may have a pulse duration in the range of 1 as to 1 ms, preferably 1 fs to 100 nm. Within this range, the application of the pulsed laser energy causes less damage to the target samples on the substrate. For example, when the pulsed laser is applied to desired points of the substrate, pulsed laser ablation or radiation pressure ejection takes place to completely evaporate the energy-absorbing layer or evaporate only the upper portion of the energy-absorbing layer, with the result that the target samples loaded on the energy-absorbing layer are separated alone or together with the energy-absorbing layer from the substrate. As a result, the separated target samples are detached in the direction opposite to the application direction of the pulsed laser.

4. Capture of Hydrogel Blocks

FIG. 7 shows the capture of hydrogel blocks formed by the method illustrated in FIGS. 3 and 5. Specifically, as shown in the left image of FIG. 7, a patterned pulsed laser such as patterned blue light was irradiated onto specific hydrogel blocks of the hydrogel block array formed on the energy-absorbing layer to capture individual hydrogels. The right image of FIG. 7 shows that hydrogel blocks were separated and rendered invisible and the energy-absorbing layer was evaporated along the pattern of the pulsed laser, leaving its trace.

5. Screening

FIG. 8 shows the results of screening conducted by the methods of FIGS. 1, 4, and 6. Referring to FIG. 1, a suspension of bacterial samples carrying DNA libraries in the form of bacteriophage viruses coding for antibody proteins was introduced into microreaction chambers formed by assembly of the microstructure and the substrate to induce the growth of the cells. As the cells grow in the microreaction chambers, the phage viruses surface labeled with the antibody proteins are secreted as cell products and are bound to and captured on the surfaces of the microstructure and the substrate forming the microreaction chambers based on affinity of the antibodies for target antigens. Referring to FIG. 4, when a fluorescently labeled antibody commonly binding to the viruses used in the screening experiment was used, the virus molecules labeled with antibodies having high affinity for antigens were detected on the surfaces of the microstructure. Referring to FIG. 8, the virus molecules labeled with the antibodies having high affinity shown in FIG. 4 were used to recognize their locations on the microstructure, the virus molecules at the corresponding locations were separated from the capture surfaces of the microstructure and the counterpart substrate, and gene amplification was conducted on the 96 antibody heavy chain regions by the method of FIG. 6.

The amplification of DNA carried in the separated virus molecule samples can be performed by an enzymatic reaction such as PCR based on the dissociation of surface proteins of the virus molecules (FIG. 8). Alternatively, the DNA amplification may be performed by amplification of the virus molecules via infection without an additional enzymatic reaction. To this end, the separated viruses are cultured with bacterial cells. Alternatively, when bacterial cells are captured and separated as samples containing library DNA, the DNA may be amplified by increasing the number of the cells through simple culture. The DNA amplification for analyzing library information and capturing DNA samples derived from single cells can also apply for cells and cell products obtained based on surface adsorption (FIG. 2) and in the form of hydrogel blocks (FIG. 3).

6. Analysis of Entire scFv Sequences of all Barcoded Samples by NGS

FIG. 9 shows the entire scFv sequences of all samples obtained by NGS after barcoded PCR of the VH and VL regions of single chain variable fragments (scFvs) shown in FIG. 1 and barcoding based on the barcode data. For example, scFv antibodies consisting of VH region-linker-VL region may be sequenced by the following procedure. First, (a) primer DNAs are provided to amplify specific target regions, including VH region, VL region or linker. The DNAs provided in (a) have additional sequences that can be used as barcode data. Thus, DNA amplification products can be produced in which different barcode data are linked to the individual different DNA samples. In addition to the barcode sequences, sequencing adapter sequences may be further provided for sequencing. Then, (b) the DNA amplification products of different target regions obtained from the different samples are pooled, followed by parallel sequencing such as next generation sequencing. Thereafter, (c) the sequencing results are sorted based on the barcode data and the sequencing results of the target regions derived from the same sample are linked to obtain the entire sequence information of the sample DNA. In the case where the length of the DNA of interest is shorter than the read length, the entire DNA sequence can also be analyzed by sequencing only once without the need to separately sequence specific target regions. For instance, since scFv molecules as typical analytes in antibody studies consist of DNA sequences, each of which contains about 50-500 VH regions and about 50-500 VL regions, the sequences of all regions can be identified by connecting the sequences of two or more target regions with shorter sequence lengths.

7. Reading of Barcode Data to Obtain the Entire scFv Sequences of all Barcoded Samples by NGS FIG. 10 shows the results of barcode data reading to obtain the entire scFv sequences of all barcoded samples based on barcode data by NGS after barcoded PCR of the VH and VL regions of single chain variable fragments (scFvs) in FIGS. 1 and 9. Specifically, FIG. 10 shows the results of 300×2 NGS readings using a sequencer (Miseq, Illumina) after barcoded PCR on 480 different cell and virus samples (96 well barcodes×5 plate barcodes). The presence of about 350 and 450 DNA base pairs in the VL and VH regions of the scFv molecules, respectively, indicate that the antibody sequences and the barcoded fragments were successfully read with 300×2 readings. About 10,000 barcode readings were scanned for the 480 sample barcodes.

8. Identification of Information on Antibody Amino Acids in Constituent VL and VH Regions of scFv Antibody Obtained from the Entire scFv Sequences of all Barcoded Samples Analyzed by NGS

INDUSTRIAL APPLICABILITY

The technique of the present invention is applicable to various kinds of library screening for analyzing various phenotypic changes resulting from different sequences of DNAs in a DNA library, compared to the conventional technique. For example, the technique of the present invention may be utilized to find optimal conditions for microbial mutation in the field of metabolic engineering to investigate optimal microbial genetic transformation for biofuel production in maximum yields. In addition, biological reaction products separated by the technique of the present invention can be effectively used to find significant antibodies by comparison with products obtained by existing antibody screening methods including cloning using microorganisms or products obtained by library analysis techniques such as next-generation sequencing.

The invention claimed is:
1. A biological sample analysis chip comprising:
a microstructure-based analysis chip;
a substrate-based analysis chip; and
an array of microreaction chambers defined by the microstructure-based analysis chip and the substrate-based analysis chip,
wherein at least one of the microstructure-based analysis chip and the substrate-based analysis chip is configured to capture library-carrying cells and/or library-carrying cell products formed by biochemical reactions of the cells,
the microstructure-based analysis chip and the substrate-based analysis chip are detachable from each other and separately analyzable, and
the biological sample analysis chip further comprises an energy-absorbing layer, wherein the energy-absorbing layer is configured such that target samples located on sites of the energy-absorbing layer to which energy is applied; are separated from the microstructure-based analysis chip or the substrate-based analysis chip upon the energy application.

2. The biological sample analysis chip according to claim 1, wherein one or more selected from the group consisting of the same library-carrying cells and the same library-carrying cell products formed by biochemical reactions of the cells are captured on one of the surfaces of the microstructure-based analysis chip and the substrate-based analysis chip or are captured in the form of hydrogel blocks on one of the surfaces of the microstructure-based analysis chip and the substrate-based analysis chip.

3. The biological sample analysis chip according to claim 2, wherein one of the microstructure-based analysis chip and the substrate-based analysis chip is used to characterize the captured cell products and/or cells and the other analysis chip is used to determine the locations of the captured cell products and/or cells and separate the captured cell products and/or cells for sample provision.

4. The biological sample analysis chip according to claim 1, wherein one of the microstructure-based analysis chip and the substrate-based analysis chip is used to characterize the captured cell products and/or cells and to determine the locations of the captured cell products and/or cells and separate the captured cell products and/or cells for sample provision.

5. The biological sample analysis chip according to claim 4, wherein the location determination enables analysis of information on the location of the cell products or the cells to be separated for sample provision by providing a reference mark on the microstructure-based analysis chip or the substrate-based analysis chip.

6. The biological sample analysis chip according to claim 5, wherein location information of the microstructure or the reference mark in images of the analysis chips obtained before or after detachment of the analysis chips is used to provide the locations of the same library-carrying cell products or the same library-carrying cells on the microstructure-based analysis chip and the substrate-based analysis chip.

7. The biological sample analysis chip according to claim 1, wherein at least one of the microstructure-based analysis chip and the substrate-based analysis chip further comprises a target-capture layer.

8. The biological sample analysis chip according to claim 1, wherein at least one of the microstructure-based analysis chip and the substrate-based analysis chip further comprises an adhesion controlling layer.

9. The biological sample analysis chip according to claim 1, wherein the microstructure-based analysis chip and the substrate-based analysis chip are used for antibody library screening or multiple genetic and/or phenotypic analysis of biochemical molecules.

10. A method for preparing the biological sample analysis chip of claim 1, comprising: spatially dividing, isolating, and arranging samples comprising library-carrying cells; and performing biochemical reactions of the cells, wherein the samples are isolated and arranged such that cell products produced by the biochemical reactions and the cells are captured using a number of closed reaction chambers formed by assembly of a microstructure and a substrate or some or all of the surfaces surrounding the reaction chambers.

11. The method according to claim 10, wherein the substrate is selected from a second microstructure different from the microstructure, a flat plate, a film, a net-shaped flat plate or film through which the samples selectively pass, and combinations thereof.

12. The method according to claim 10, wherein the biochemical reactions are performed using a biochemical liquid preparation under conditions for growing the cells, for inducing apoptosis or cell membrane disruption or for secreting the cell products comprising virus molecules.

13. The method according to claim 10, wherein the cell products produced by the biochemical reactions and the cells are captured on the surface(s) of the microstructure and/or the surface of the substrate surrounding the samples and the reaction chambers based on the principle of adsorption or binding by intermolecular binding or sample-surface interaction comprising van der Waals forces, hydrophobic interaction, electrostatic force or affinity.

14. The method according to claim 13, wherein at least one of the microstructure and the substrate comprises a base and a target-capture layer formed on the base.

15. The method according to claim 14, wherein an energy-absorbing layer is formed between the target-capture layer and the base.

16. The method according to claim 10, wherein the cell products produced by the biochemical reactions and the cells are captured on the surfaces of the microstructure and/or the surface of the substrate surrounding the closed reaction chambers based on the principle of adsorption or binding by drying of the biochemical liquid preparation, lyophilization or sample-surface interaction.

17. The method according to claim 10, wherein after the isolation/arrangement and the biochemical reactions, the microstructure and the substrate forming the closed reaction chambers are detached from each other to provide an analysis chip set in which the same library-carrying cell products and/or cells are obtained on the microstructure or the substrate.

18. The method according to claim 17, wherein the analysis chip set is used to analyze the biochemical and physiological properties of library constructs contained in the reaction chambers or the sequences of the library constructs and/or to selectively separate the captured samples.

19. The method according to claim 18, wherein the isolation/arrangement and the biochemical reactions are performed by introducing a hydrogel-forming material into the reaction chambers then by gelling the material, and the gelling of the hydrogel-forming material forms hydrogels on the surfaces of the microstructure or the surface of the substrate.

20. The method according to claim 19, wherein at least one of the microstructure and the substrate comprises either or both an energy-absorbing layer and an adhesion controlling layer formed on a base.

21. The method according to claim 19, wherein the cells present in the hydrogels formed on the surfaces of the microstructure or the substrate are used to analyze the sequences, biochemical properties, and physiological properties of the library constructs or to selectively separate the captured samples.

* * * * *